United States Patent [19]
Yoshino

[11] Patent Number: 5,741,922
[45] Date of Patent: Apr. 21, 1998

[54] FLUORINE-CONTAINING AROMATIC COMPOUNDS

[75] Inventor: Norio Yoshino, Mitaka, Japan

[73] Assignee: Daikin Industries, Ltd., Osaka, Japan

[21] Appl. No.: 525,702

[22] PCT Filed: Mar. 9, 1994

[86] PCT No.: PCT/JP94/00374

§ 371 Date: Sep. 12, 1995

§ 102(e) Date: Sep. 12, 1995

[87] PCT Pub. No.: WO94/20442

PCT Pub. Date: Sep. 15, 1994

[30] Foreign Application Priority Data

Mar. 12, 1993 [JP] Japan ................................. 5-078704

[51] Int. Cl.$^6$ ........................................................ C07F 7/08
[52] U.S. Cl. .................. 556/445; 556/485; 252/62.51; 252/62.55; 252/62.64; 428/447; 428/450; 428/457; 428/403
[58] Field of Search .................. 556/445, 485; 252/62.51, 62.55, 62.64; 428/447, 450, 457, 403

[56] References Cited

U.S. PATENT DOCUMENTS

| | | | |
|---|---|---|---|
| 5,068,387 | 11/1991 | Kleyer et al. | 556/485 |
| 5,545,255 | 8/1996 | Ogawa | 556/485 X |

FOREIGN PATENT DOCUMENTS

| | | |
|---|---|---|
| 57-142923 | 9/1982 | Japan . |
| 58-188833 | 11/1983 | Japan . |
| 61-91138 | 5/1986 | Japan . |
| 61-212526 | 9/1986 | Japan . |
| 62-109884 | 5/1987 | Japan . |
| 1316359 | 12/1989 | Japan . |
| 2200646 | 8/1990 | Japan . |
| 3106889 | 5/1991 | Japan . |
| 3218325 | 9/1991 | Japan . |
| 5159917 | 6/1993 | Japan . |

OTHER PUBLICATIONS

R.A., Benkeser, "Silylation of organic halides. New method of forming the carbon–silicon bond.", A. Amer. Chem. Soc. 1969, 91(13), 3666–7 (Eng), vol. 71, No. 13, Sep. 29, 1969.

*Primary Examiner*—Paul F. Shaver
*Attorney, Agent, or Firm*—Loeb & Loeb LLP

[57] ABSTRACT

A fluorine-containing aromatic compound represented by the formula (1) is effectively usable to obtain a magnetic fluid or the like having a wide heat-resistant temperature range and high water resistance

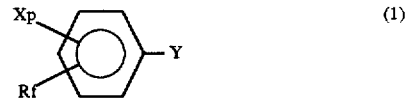

(1)

wherein X is H, F, Cl, $C_{1-20}$ alkyl or $C_{1-20}$ alkoxyl, p is an integer of 1 to 4, Y is —$COCH_3$, —$COOC_2H_5$, —$CH(OH)CH_3$, —$C(CH_3)_2OH$, —$CH=CH_2$, —$C(CH_3)=CH_2$, —$CAB(CH_2)_mSi(CH_3)_nZ_{3-n}$, A and B are each H or $CH_3$, Z is Cl, $OCH_3$ or $OC_2H_5$, and m and n are each 0 or 1, and Rf is $C_{1-20}$ fluoroalkyl or $C_{1-100}$ fluoropolyether group.

6 Claims, No Drawings

FLUORINE-CONTAINING AROMATIC COMPOUNDS

TECHNICAL FIELD

The present invention relates to fluorine-containing aromatic compounds and silane coupling agents comprising the compound.

BACKGROUND ART

Composite materials comprising an inorganic material and an organic material in combination are presently used in various fields because of their outstanding properties and sophisticated functions. With composite materials, control of the interface between the different component materials thereof is a very important problem. As one method of control, silane coupling agents are used for modifying the surface of inorganic materials. With the introduction of fluorocarbon chains having peculiar properties such as water or oil repellency, high lubricity and chemical resistance into silane coupling agents, increased attention has been directed to the application of these agents as surface modifying agents having a function different from that of imparting improved adhesion.

For example, magnetic fluids can be obtained pulverization, deflocculation or a process involving adsorption in an aqueous solution and organic phase dispersion. In the case of any of these processes, finely divided magnetite, iron or like ferromagnetic material is given affinity for a solvent by being caused to adsorb a surfactant on the surface for modification and then dispersed in a base oil. However, the magnetic fluid incorporating the surfactant is unsatisfactory in heat resistance, cold resistance, resistance to chemicals, insulating properties, etc. Especially the surfactant used for stabilizing the dispersion of the finely divided ferromagnetic material usually has a hydrophilic group, so that when water or a highly humid gas is sealed with the magnetic fluid, water dissolves in the magnetic fluid, releasing the surfactant from the material and deteriorating the magnetic fluid. Further magnetic fluids wherein a hydrocarbon oil is used as the base oil are −20° C. to 150° C. in the range of heat-resistant temperatures, solidify in a cold climate or deteriorate in a high temperature range owing to oxidation and therefore remain to be improved.

In order to develop a magnetic fluid having a wide heat-resistant temperature range and high water resistance, we have conducted research and found that this purpose can be accomplished by modifying the surface of a finely divided magnetic material with a fluorine-containing aromatic silane coupling agent and dispersing the material is a medium, and also by using a fluorine-containing oil having a wide heat-resistant temperature range as the dispersion medium (base oil).

An object of the present invention is to provide a fluorine-containing aromatic compound which is advantageously usable for preparing a magnetic fluid or the like having a wide heat-resistant temperature range and high water resistance, and a silane coupling agent comprising the compound.

DISCLOSURE OF THE INVENTION

The present invention provides a fluorine-containing aromatic compound represented by the formula (1)

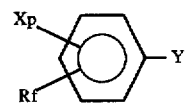

(1)

wherein X is H, F, Cl, $C_{1-20}$ alkyl or $C_{1-20}$ alkoxyl, p is an integer of 1 to 4, Y is —$COCH_3$, —$COOC_2H_5$, —$CH(OH)CH_3$, —$C(CH_3)_2OH$, —$CH=CH_2$, —$C(CH_3)=CH_2$, —$CAB(CH_2)_mSi(CH_3)_nZ_{3-n}$, A and B are each H or $CH_3$, Z is Cl, $OCH_3$ or $OC_2H_5$, and m and n are each 0 or 1, and Rf is $C_{1-20}$ fluoroalkyl or $C_{1-100}$ fluoropolyether group.

The invention also provides a fluorine-containing aromatic silane coupling agent comprising a compound of the formula (1) wherein Y is —$CAB(CH_2)_mSi(CH_3)_nZ'_{3-n}$, wherein A, B, m and n are each the same as defined above, and Z' is $OCH_3$ or $OC_2H_5$.

The invention further provides a finely divided magnetic material having its surface modified with the fluorine-containing aromatic silane coupling agent.

According to the invention, examples of $C_{1-20}$ alkyl groups are methyl, ethyl, propyl, butyl, hexyl, nonyl, dodecyl, heptadecyl, eicosyl, etc. Examples of $C_{1-20}$ alkoxyl groups are alkoxyl groups corresponding to the above-mentioned alkyl groups.

Examples of $C_{1-20}$ fluoroalkyl groups are $CF_3(CF_2)_l$—, l is 0 to 19, $(CF_3)_2CF(CF_2)_p$—, p is 0 to 17, H $(CF_2)_q$—, q is 1 to 20, etc.

Examples of $C_{1-100}$ fluoropolyether groups are $F(CF_2CF_2CF_2O)_r$—, r is 1 to 33, $F[CF_2CF(CF_3)O]_r$—, r is 1 to 33, $F[CF(CF_3)CF_2O]_s$ $(CF_2O)_t$—, s is 0 to 33, t is 0 to 100, $CF_3O(CF_2CF_2O)_u(CF_2O)_v$—, u is 0 to 49, v is 0 to 99, etc.

Among the fluorine-containing aromatic compounds of the invention, the compound of the formula wherein Y is —$CH(OH)CH_3$ is obtained, for example, by reacting a methyl magnesium halide with a fluorine-containing aromatic aldehyde of the formula (2), and hydrolyzing the resulting product

(2)

wherein X, Rf and p are each as defined above.

When further dehydrated, this compounds gives a compound of the formula (1) wherein Y is —$CH=CH_2$.

Of the fluorine-containing aromatic compound of the invention, the compound wherein Y is —$COCH_3$ is obtained, for example, by reacting an acetylphenyl bromide derivative of the formula (3) with RfD wherein Rf is as defined above, and D is a halogen atom

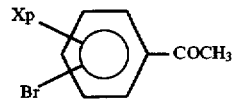

(3)

wherein X and p are each as defined above.

When subsequently reduced, this compound affords a compound wherein Y is —$CH(OH)CH_3$. When further dehydrated, this compound gives a compound wherein Y is —$CH=CH_2$.

Further the compound wherein Y is —$COOC_2H_5$ is prepared, for example, by reacting an ethyl iodobenzoate derivative of the formula (4) with RfD wherein Rf and D are each as defined above

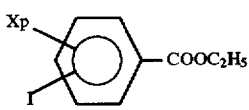

wherein X and p are each as defined above.

This compound, when reacted with a methyl magnesium halide, gives a compound wherein Y is —C(CH$_3$)$_2$OH, which affords a compound wherein Y is —C(CH$_3$)=CH$_2$ when further dehydrated.

The compound wherein Y is —CAB(CH$_2$)$_m$Si(CH$_3$)$_n$Cl$_{3-n}$ is obtained, for example, by reacting a styrene derivative of the formula (5) with HSi(CH$_3$)$_n$Cl$_{3-n}$

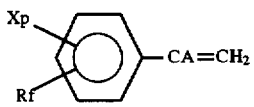

wherein X, p, Rf and A are each as defied above.

When subsequently reacted with sodium methoxide, this compound gives a compound wherein Y is —CAB(CH$_2$)$_m$Si(CH$_3$)$_n$(OCH$_3$)$_{3-n}$.

Typical examples of the foregoing reactions are, for example, as follows when expressed by chemical reaction equations.

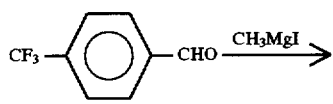

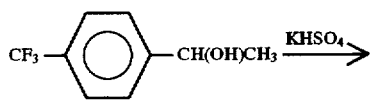

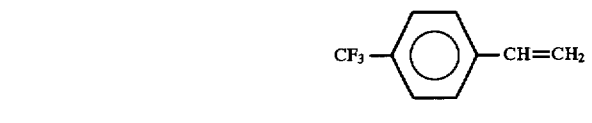

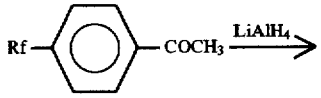

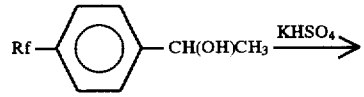

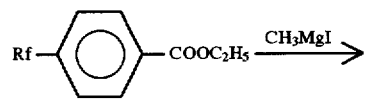

-continued

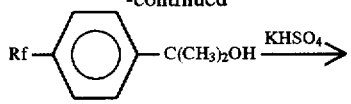

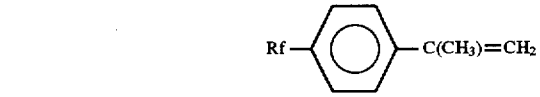

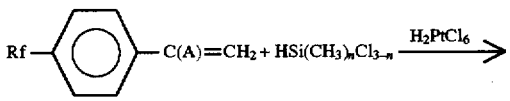

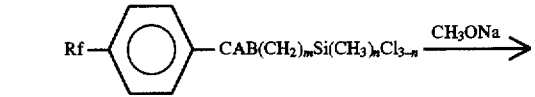

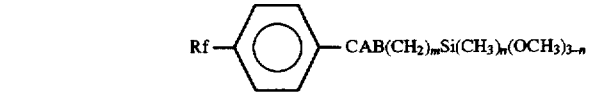

The above compounds can be separated off and purified by usual known methods such as extraction, concentration, distillation, recrystallization and chromatography.

Of the foregoing compounds of the present invention, those wherein Y is —CAB(CH$_2$)$_m$Si(CH$_3$)$_n$Z'$_{3-n}$ are useful as silane coupling agents. These fluorine-containing aromatic silane coupling agents are usable, for example, for modifying the surface of particulate magnetic materials. A magnetic fluid can be obtained by dispersing the modified particulate magnetic material in a dispersion medium (base oil).

The particulate magnetic material can be any kind of magnetic powder such as magnetite, maghemite, samarium-cobalt, or iron nitride powder. Examples of useful dispersion media are methanol, ethanol, n-propanol, isopropanol and like alcohols represented by C$_w$H$_{2w+1}$OH wherein w is 1 to 18, acetone, methyl ethyl ketone, methyl isobutyl ketone and like ketones, ethyl acetate, butyl acetate and like esters, n-hexane, isooctane, heptane, industrial gasoline, toluene, xylene and like hydrocarbons, naphthalene, naphthalenes and like liquid compounds having a naphthalene skeleton and one or two C$_{1-20}$ alkyl groups as substituents, trichlorotrfluoroethane (F-113), poly(chlorotrifluoroethylene) (PCTFE) [brand name, Daifloil, product of Daikin Industries, Ltd.], perfluoropolyether [brand name, Demnum, product of Daikin Industries, Ltd., brand name, Krytox, product of E. I. du Pont de Nemours & Co., brand name, Fomblin, product of Montefluous] and like fluorine-containing oils. Especially preferable are fluorine-containing oils which have a wide heat-resistant temperature range.

For magnetic particles to be present in the dispersion medium with stability in preparing the magnetic fluid, the magnetic particles need to be prevented from coagulating in the steps of preparation process, and the surfaces of the particles as finely divided must be modified with the fluorine-containing aromatic silane coupling agent. For this purpose, we have found it effective, for example, to treat the surfaces of the magnetic particles with a surfactant and then contact the particle surfaces with the silane coupling agent to replace the surfactant adsorbed on the particle surfaces by the silane coupling agent. Examples of useful surfactants are oleic acid, stearic acid, myristic acid, aerosol OT (AOT), nonyl phenyl ethers and fluorine-containing surfactants.

According to the present invention, the fluorine-containing aromatic silane coupling agent is reacted with a magnetic fluid wherein fine magnetic particles are present as stably dispersed. With oleic acid or like surfactant adsorbed on the particles, whereby the surfactant is released from the particles, permitting the coupling agent to be bonded to the particles which remain small in size. We have found that this method releases a major portion of the surfactant (99% in the case of oleic acid), nearly quantitatively replacing the surfactant by the coupling agent. The surfactant is adsorbed by the surfaces of the magnetic particles, allowing the particles to be dispersed in the solvent, but is held adsorbed in equilibrium. It is thought that fluorine-containing aromatic silane coupling agent combines with hydroxyl on the particle surface by a covalent bond and therefore does not become released when once bonded, and that the replacement occurs successively, liberating almost the entire amount of surfactant. Since the magnetic particles obtained by this method are readily dispersible in F-113, PCTFE and like fluorine-containing oils, it appears that they remain very small in size (4–7 nm, mean particle size 5.5 nm). When the surfactant was not used for modification, the fluorine-containing aromatic silane coupling agent combined with the surfaces of agglomerates, and it was impossible to modify the surfaces of fine particles.

BEST MODE FOR CARRYING OUT THE INVENTION

The invention will be described below in detail with reference to examples.

EXAMPLE 1

Magnesium (3.71 g/0.153 mol) was placed into a flask of the egg-plant type, followed by the replacement of air by nitrogen and addition of 30 ml of ether. While gently stirring the mixture, a solution of methyl iodide (24.4 g/0.172 mol) in ether (20 ml) was slowly added dropwise to the mixture, and the resulting mixture was refluxed with heating for 30 minutes. The mixture was cooled to room temperature, and a solution of 4-trifluoromethylbenzaldehyde (25.1 g/0.144 mole) in ether (20 ml) was slowly added dropwise to the mixture. The mixture was refluxed with heating for 2 hours, 30 ml of water was added dropwise to the mixture with ice cooling, and hydrochloric acid (2N) was further added until the aqueous layer became transparent. The aqueous layer was separated from an ethereal layer, the aqueous layer was subjected to extraction with ether, and the ethereal layers were combined, and the combined layer was washed with an aqueous solution of common salt three times. After removal of ether, the layer was distilled at a reduced pressure, giving 1-(1-hydroxylethyl)-4-trifluoromethylbenzene [compound (I)] represented by the formula $CF_3C_6H_4CH(OH)CH_3$, b.p. 53°~55° C. (50.5 Pa), colorless transparent liquid, yield 98.3%.

EXAMPLE 2

To the compound (I) (27.0 g/0.142 mol) were added potassium hydrogensulfate (7 g) and 4-tert-butylcatechol (polymerization inhibitor, 0.01 g). The mixture was distilled at 150° to 180° C. using an oil bath to collect the whole distillate. Ether (20 ml) was added to the distillate, an ethereal layer was separated from water, and sodium sulfate was added to the layer for dehydration, followed by filtration. The ether was removed from the filtrate, to which 4-tert-butylcatechol was added again. The filtrate was then distilled at a reduced pressure, giving 4-trifluoromethylstyrene [compound (II)] represented by the formula $CF_3C_6H_4CH=CH_2$, b.p. 78°~80° C. (2660 Pa), colorless transparent liquid, yield 76.5%.

EXAMPLE 3

$CF_3(CF_2)_3I$ (24.5 g), 4'-bromoacetophenone (14.1 g), Cu powder (24.4 g) and dimethyl sulfoxide (DMSO, 45 ml) were placed into a flask of the egg-plant type equipped with a reflux tube and were reacted at 110° C. for 20 hours in a nitrogen stream. The reaction mixture was cooled to room temperature, and an excess of the Cu powder was removed from the mixture by suction filtration. Water and ether, each in an amount of 50 ml, were added to the filtrate, followed by suction filtration again. The resulting filtrate was separated into an aqueous layer and an ethereal layer, the aqueous layer was subjected to extraction with ether, and the resulting ethereal layer was added to the ethereal layer. The combined layer was washed with an aqueous solution of common salt about three times. The ether was removed from the layer, and the residue was distilled at a reduced pressure, giving a perfluoroalkyl-substituted benzophenone represented by $CF_3(CF_2)_3C_6H_4COCH_3$, b.p. 55°~58° C. (43.9 Pa), colorless transparent liquid, yield 92.5%.

EXAMPLE 4

The procedure was repeated in the same manner as in Example 3 except that $CF_3(CF_2)_7I$ was used as a perfluoroalkyliodide compound to obtain a perfluoroalkyl-substituted benzophenone represented by $CF_3(CF_2)_5C_6H_4COCH_3$, b.p. 78°~80° C. (22.6 Pa), m.p. 48°~49° C., white solid, yield 91.8%.

EXAMPLE 5

The procedure was repeated in the same manner as in Example 3 except that $CF_3(CF_2)_7I$ was used as a perfluoroalkyliodide compound to obtain a perfluoroalkyl-substituted benzophenone represented by $CF_3(CF_2)_7C_6H_4COCH_3$, b.p. 102°~105° C. (35.9 Pa), m.p. 63.5°~64° C., white solid, yield 93.5%.

EXAMPLE 6

In a nitrogen atmosphere, $LiAlH_4$ (1.29 g) was placed into a flask of the egg-plant type and suspended in 30 ml of ether. A solution of the $CF_3(CF_2)_3C_6H_4COCH_3$ (22.1 g) obtained in Example 3 in ether was slowly added dropwise to the suspension with stirring, and the mixture was refluxed with heating for 30 minutes. Water was added to the reaction mixture with ice cooling until $H_2$ ceased to evolve, and 10% aqueous solution of sulfuric acid was added to the mixture until a white precipitate [$Al(OH)_3$] dissolved. The resulting mixture was separated into an aqueous layer and an ethereal layer, the aqueous layer was subjected to extraction with ether, and the resulting ethereal layer was added to the ethereal layer. The combined layer was washed with an aqueous solution of common salt, ether was removed from the layer, and the resulting residue was distilled at a reduced pressure, giving a compound represented by the formula $CF_3(CF_2)_3C_6H_4CH(OH)CH_3$, b.p. 69°~70° C. (23.9 Pa), colorless transparent liquid, yield 98.7%.

EXAMPLE 7

The procedure was repeated in the same manner as in Example 6 with the exception of using $CF_3(CF_2)_5C_6H_4COCH_3$ obtained in Example 4 to prepare a compound represented by the formula $CF_3(CF_2)_5C_6H_4CH(OH)CH_3$, b.p. 98°~102° C. (66.5 Pa), m.p. 46°~47.5° C., white solid, yield 98.2%.

EXAMPLE 8

The procedure was repeated in the same manner as in Example 6 with the exception of using $CF_3(CF_2)_7$ $C_6H_4COCH_3$ obtained in Example 5 to prepare a compound represented by the formula $CF_3(CF_2)_7C_6H_4CH(OH)CH_3$, b.p. 92°~93° C. (28.6 Pa), m.p. 58.5°~59° C., white solid, yield 98.6%.

EXAMPLE 9

In a nitrogen atmosphere, toluene and potassium hydrogensulfate (8 g) were added to the $CF_3(CF_2)_3C_6H_4CH(OH)CH_3$ (22.7 g) obtained in Example 6. The mixture was stirred with heating at 95° C. for 18 hours using an oil bath. After cooling, the mixture was distilled at a reduced pressure with addition of 4-tert-butylcatechol (polymerization inhibitor, 0.01 g), giving a perfluoroalkylstyrene compound represented by the formula $CF_3(CF_2)_3C_6H_4CH=CH_2$, b.p. 46.5°~48° C. (33.3 Pa), colorless transparent liquid, yield 90.2%.

EXAMPLE 10

The procedure was repeated in the same manner as in Example 9 with the exception of using $CF_3(CF_2)_5C_6H_4CH(OH)CH_3$ obtained in Example V to prepare a perfluoroalkylstyrene compound represented by the formula $CF_3(CF_2)_5C_6H_4CH=CH_2$, b.p. 63°~65° C. (32 Pa), colorless transparent liquid, yield 90.8%.

EXAMPLE 11

The procedure was repeated in the same manner as in Example 9 with the exception of using $CF_3(CF_2)_7C_6H_4CH(OH)CH_3$ obtained in Example 8 to prepare a perfluoroalkylstyrene compound represented by the formula $CF_3(CF_2)_7C_6H_4CH=CH_2$, b.p. 75°~76° C. (32.6 Pa), colorless transparent liquid, yield 88.4%.

EXAMPLE 12

$CF_3(CF_2)_3I$ (14.1 g), ethyl 4-iodobenzoate (10.9 g), Cu powder (8.89 g) and DMSO (35 ml) were placed into a flask of the egg-plant type equipped with a reflux tube and were reacted at 110° C. for 18 hours under a nitrogen stream. The reaction mixture was cooled to room temperature, and an excess of the Cu powder was removed from the mixture by suction filtration. Water and ether, each in an amount of 50 ml, were added to the filtrate, followed by suction filtration again. The resulting filtrate was separated into an aqueous layer and an ethereal layer, the aqueous layer was subjected to extraction with ether, and the resulting ethereal layer was added to the ethereal layer. The combined layer was washed with an aqueous solution of common salt about three times. After removal of ether from the layer, the residue was distilled at a reduced pressure, giving an ethyl perfluoroalkyl-substituted benzoate represented by the formula $CF_3(CF_2)_3C_6H_4COOC_2H_5$, b.p. 63°~65° C. (62.5 Pa), colorless transparent liquid, yield 88.9%.

EXAMPLE 13

The procedure was repeated in the same manner as in Example 12 except that $CF_3(CF_2)_5I$ was used as a perfluoroalkyliodide compound to obtain a perfluoroalkyl-substituted ethyl benzoate represented by the formula $CF_3(CF_2)_5C_6H_4COOC_2H_3$, b.p. 77°~79° C. (26.6 Pa), m.p. 28°~29° C., white solid, yield 90.3%.

EXAMPLE 14

The procedure was repeated in the same manner as in Example 12 except that $CF_3(CF_2)_7I$ was used as a perfluoroalkyliodide compound to obtain a perfluoroalkyl-substituted ethyl benzoate represented by the formula $CF_3(CF_2)_7C_6H_4COOC_2H_5$, b.p. 100°~102° C. (23.9 Pa), m.p. 61.5°~63° C., white solid, yield 74.5%.

EXAMPLE 15

Magnesium (4–15 g) was placed into a flask of the egg-plant type, followed by the replacement of air by nitrogen and addition of 30 ml of ether. While gently stirring the mixture, a solution of methyl iodide (26.6 g) in ether (10 ml) was slowly added dropwise to the mixture, and the resulting mixture was refluxed with heating for 30 minutes. To the mixture was slowly added dropwise a solution of $CF_3(CF_2)_3C_6H_4COOC_2H_5$ (24.6 g) obtained in Example 12 in ether (30 ml). The mixture was refluxed with heating for 2 hours, 50 ml of water was added dropwose to the mixture with ice cooling, and hydrochloric acid (2N) was further added until the aqueous layer became transparent. The aqueous layer was separated from an ethereal layer, the aqueous layer was subjected to extraction with ether, and the ethereal layers were combined, and the combined layer was washed with an aqueous solution of common salt three times. After removal of ether, the layer was distilled at a reduced pressure, giving a compound represented by the formula $CF_3(CF_2)_3C_6H_4C(CH_3)_2OH$, b.p. 69°~70° C. (23.9 Pa), colorless transparent liquid, yield 98.2%.

EXAMPLE 16

The procedure was repeated in the same manner as in Example 15 except that $CF_3(CF_2)_5C_6H_4COOC_2H_5$ was used as a perfluoroalkyl-substituted ethyl benzoate to obtain a compound represented by the formula $CF_3(CF_2)_5C_6H_4C(CH_3)_2OH$, b.p. 98°~102° C. (66.5 Pa), m.p. 57.5°~58.5° C., white solid, yield 93.1%.

EXAMPLE 17

The procedure was repeated in the same manner as in Example 15 except that $CF_3(CF_2)_7C_6H_4COOC_2H_5$ was used as a perfluoroalkyl-substituted ethyl benzoate to obtain a compound represented by the formula $CF_3(CF_2)_7C_6H_4C(CH_3)_2OH$, b.p. 92°~93° C. (28.6 Pa), m.p. 68°~69° C., white solid, yield 94.7%.

EXAMPLE 18

In a nitrogen atmosphere, potassium hydrogensulfate (8 g) was added to the $CF_6(CF_2)_3C_6H_4C(CH_3)_2OH$ (22.7 g) obtained in Example 15. The mixture was stirred with heating at 95° C. for 18 hours using an oil bath. After cooling, the mixture was distilled at a reduced pressure with addition of 4-tert-butylcatechol (polymerization inhibitor, 0.01 g), giving a perfluoroalkylmethylstyrene compound represented by the formula $CF_3(CF_2)_3C_6H_4C(CH_3)=CH_2$, b.p. 46.5°~48° C. (33.3 Pa), colorless transparent liquid, yield 90.2%.

EXAMPLE 19

The procedure was repeated in the same manner as in Example 18 with the exception of using $CF_3(CF_2)_5C_6H_4C(CH_3)_2OH$ obtained in Example 16 to prepare a perfluoroalkylmethlstyrene compound represented by the formula $CF_3(CF_2)_5C_6H_4C(CH_3)=CH_2$, b.p. 63°~65° C. (32 Pa), colorless transparent liquid, yield 90.8%.

EXAMPLE 20

The procedure was repeated in the same manner as in Example 18 with the exception of using $CF_3(CF_2)_7C_6H_4C(CH_3)_2OH$ obtained in Example 16 to prepare a perfluoroalkylmethlstyrene compound represented by the formula $CF_3(CF_2)_7C_6H_4C(CH_3)=CH_2$, b.p. 75°~76° C. (32.6 Pa), colorless transparent liquid, yield 88.4%.

EXAMPLES 21 TO 34

The styrene compopund (A), $CF_3(CF_2)_mC_6H_4C(Q)=CH_2$, and the silane compound (B), $HSi(CH_3)_nCl_{3-n}$, which are listed in Table 1 and $H_2PtCl_6$ were used to prepare a compound (III) (β-position adduct) represented by the formula $CF_3(CF_2)_mC_6H_4CH(Q)CH_2Si(CH_3)_mCl_{3-n}$ and a compound (IV) (α-position adduct) represented by the formula $CF_3(CF_2)_nC_6H_4C(Q)(CH_3)Si(CH_3)_mCl_{3-m}$. The reaction was conducted at 100° C. for 50 hours, and the reaction mixture was distilled at a reduced pressure in a nitrogen stream to obtain the desired products. The compound (III) and (IV) are useful as silane coupling agents.

was slowly added dropwise to a solution of sodium methoxide in methanol while refluxing the solution with heating, followed by continued refluxing for 1 hour. The methanol was removed from the reaction mixture at a reduced pressure. 1,1,2-trichloro-1,2,2-trifluoroethane (or carbon tetrachloride) was added to the residue, and the mixture was filtered in a nitrogen atmosphere using a glass filter (No.4). The 1,1,2-trichloro-1,2,2-trifluoroethane (or carbon tetrachloride) was removed from the filtrate. Distillation of the residue at a reduced pressure gave the desired product. The compounds (V) and (VI) are also useful as silane coupling agents.

TABLE 1

| Ex. | Compound A (g) | Compound B (g) | $H_2PtCl_6$ (ml) | yield (%) | b.p. (°C./Pa) | III/IV |
|---|---|---|---|---|---|---|
| 21 | m = 0, Q = H 9.74 | n = 1 9.73 | 0.2 | 89.0 | 126~129/ 1060~1730 | 87/13 |
| 22 | m = 3, Q = H 10.4 | n = 1 6.37 | 0.15 | 76.4 | 86~90/ 53~47 | 91/9 |
| 23 | m = 5, Q = H 22.4 | n = 1 10.1 | 0.15 | 88.4 | 100~102/ 76 | 90.5/9.5 |
| 24 | m = 7, Q = H 18.9 | n = 1 8.38 | 0.15 | 87.1 | 104.5~106/ 31 | 90/10 |
| 25 | m = 3, Q = $CH_3$ 8.91 | n = 1 4.74 | 0.15 | 90.4 | 84~87.5/ 27 | 98/2 |
| 26 | m = 5, Q = $CH_3$ 8.27 | n = 1 3.82 | 0.15 | 86.2 | 84~94/ 39~43 | 97/3 |
| 27 | m = 7, Q = $CH_3$ 5.97 | n = 1 2.64 | 0.1 | 63.9 | 112~113/ 27 | 100/0 |
| 28 | m = 0, Q = H 14.3 | n = 0 16.1 | 0.2 | 74.9 | 108~125/ 1460~1730 | 78/22 |
| 29 | m = 3, Q = H 10.1 | n = 0 6.71 | 0.1 | 90.2 | 98/39 | 95/5 |
| 30 | m = 5, Q = H 19.8 | n = 0 9.64 | 0.2 | 93.1 | 101~102/ 39 | 94/6 |
| 31 | m = 7, Q = H 11.4 | n = 0 5.20 | 0.15 | 90.2 | 120~123/ 35 | 92.5/7.5 |
| 32 | m = 3, Q = $CH_3$ 7.91 | n = 0 6.22 | 0.2 | 91.2 | 80~83/ 39 | 66/34 |
| 33 | m = 5, Q = $CH_3$ 23.0 | n = 0 10.0 | 0.3 | 68.7 | 102~105/ 44 | 87/13 |
| 34 | m = 7, Q = $CH_3$ 7.02 | n = 0 3.11 | 0.05 | 73.0 | 106.5~109/ 31 | 90.5/9.5 |

EXAMPLES 35 TO 48

The silane coupling agent (C) [mixture of compounds (I) and (IV)] given in Table 2 and $CH_3ONa$ were used to prepare a mixture of a compound (V) (β-position adduct) represented by the formula $CF_3(CF_2)_mC_6H_4CH(Q)CH_2Si(CH_3)_n(OCH_3)_{3-n}$ and a compound (VI) (α-position adduct) represented by the formula $CF_3(CF_2)_mC_6H_4C(Q)(CH_3)Si(CH_3)_n(OCH_3)_{n-3}$. For reaction, the silane coupling agent

TABLE 2

| Example | Compound C (g) | | $CH_3ONa$ (ml) | yield (%) | b.p. (°C./Pa) |
|---|---|---|---|---|---|
| 35 | m = 0, Q = H | n = 1 (10.7) | 35 | 65.0 | 97~105/1330 |
| 36 | m = 3, Q = H, | n = 1 (4.52) | 10 | 67.0 | 87.5~89/46.6 |
| 37 | m = 5, Q = H, | n = 1 (7.10) | 20 | 76.0 | 89~92/33.3 |
| 38 | m = 7, Q = H, | n = 1 (7.98) | 12 | 82.0 | 103~105/43.9 |
| 39 | m = 3, Q = $CH_3$, | n = 1 (8.82) | 17 | 90.7 | 81~83/50.5 |
| 40 | m = 5, Q = $CH_3$, | n = 1 (6.85) | 12 | 85.7 | 94~97/51.9 |
| 41 | m = 7, Q = $CH_3$, | n = 1 (4.02) | 5.5 | 28.1 | 96~97/29.3 |
| 42 | m = 0, Q = H, | n = 0 (12.0) | 44 | 67.6 | 133~139/2530 |
| 43 | m = 3, Q = H, | n = 0 (10.8) | 27 | 62.8 | 87~90/66.5 |
| 44 | m = 5, Q = H, | n = 0 (22.2) | 45 | 75.3 | 107~115/93.1 |
| 45 | m = 7, Q = H, | n = 0 (11.0) | 19 | 72.2 | 111~116/50.5 |
| 46 | m = 3, Q = $CH_3$, | n = 0 (8.96) | 22 | 77.4 | 93~95/42.6 |
| 47 | m = 5, Q = $CH_3$, | n = 0 (19.2) | 38 | 88.9 | 66~70/29.3 |
| 48 | m = 7, Q = $CH_3$, | n = 0 (6.96) | 12 | 82.0 | 91~93/29.3 |

TEST EXAMPLE 1

(Water and Oil Repellency Test)

The compounds D to H, silane coupling agents, listed in Table 3 were tested for effect to modify the surface of glass.

Glass: Matsunami Slide Glass S-7214

Contact angle meter: product of Eruma Kogaku Co., Ltd.

Compound D: $CF_3(CF_2)_nC_6H_4CH_2CH_2Si(CH_3)(OCH_3)_2$

Compound E: $CF_3(CF_2)_nC_6H_4CH(CH_3)CH_2Si(CH_3)(OCH_3)_2$

Compound F: $CF_3(CF_2)_nC_6H_4CH_2CH_2Si(OCH_3)_3$

Compound G: $CF_3(CF_2)_nC_6H_4CH(CH_3)CH_2Si(OCH_3)_3$

Compound H: $CF_3(CF_2)_nCH_2CH_2Si(CH_3)(OCH_3)_2$ (The compound H is a comparative example.)

A plate of the glass was immersed in a solution of 10 mmols of the test compound in CFC-113, and the solution was heated at 47° C. for 1 hour. The glass plate was thereafter withdrawn from the solution, washed with CFC-113 and heat-treated at 200° C. for 1 hour. Thirty days thereafter, the contact angle of liquid drops, $1 \times 10^{-6} dm^3$, on the glass plate was measured under the conditions of 22°–24° C. and RH 35–40%. The water repellency of the compound was evaluated in terms of the contact angle of water, and the oil repellency thereof in terms of the contact angle of oleic acid. Table 3 shows the result.

TEST EXAMPLE 2

(Oxidation Resistance Test)

The glass plate used in Test Example 1 for measuring the contact angle was heated in a hot concentrated nitric acid at 100° C. for 2 hours for oxidation and thereafter checked for contact angle. Table 3 shows the result.

TABLE 3

| | water repellency | oil repellency | oxidation resistance | |
|---|---|---|---|---|
| | water | oleic acid | water | oleic acid |
| Compound D | | | | |
| n = 0 | 100.0 | 59.0 | 88.0 | 44.0 |
| n = 3 | 101.0 | 60.0 | 92.5 | 52.5 |
| n = 5 | 101.5 | 62.5 | 93.0 | 54.0 |
| n = 7 | 103.5 | 63.0 | 97.0 | 56.0 |
| Compound E | | | | |
| n = 3 | 100.0 | 56.0 | 78.0 | 49.0 |
| n = 5 | 101.0 | 58.0 | 80.0 | 51.0 |
| n = 7 | 101.5 | 61.0 | 82.5 | 53.0 |
| Compound F | | | | |
| n = 0 | 99.0 | 51.0 | 85.0 | 42.0 |
| n = 3 | 102.0 | 59.0 | 92.0 | 50.0 |
| n = 5 | 103.0 | 62.0 | 101.0 | 62.0 |
| n = 7 | 103.0 | 64.0 | 102.0 | 64.0 |
| Compound G | | | | |
| n = 3 | 99.5 | 59.0 | 98.0 | 57.0 |
| n = 5 | 101.0 | 62.0 | 100.0 | 59.0 |
| n = 7 | 102.5 | 65.0 | 100.5 | 60.0 |
| Compound H | | | | |
| n = 3 | 86.0 | 58.0 | 46.0 | 33.0 |
| n = 5 | 100.0 | 63.0 | 62.0 | 39.0 |
| n = 7 | 103.0 | 68.0 | 74.0 | 50.0 |

INDUSTRIAL APPLICABILITY

According to the invention, obtained are a fluorine-containing aromatic compound which is advantageously usable for preparing a magnetic fluid or the like having a wide heat-resistant temperature range and high water resistance, and a silane coupling agent comprising the compound.

I claim:

1. A fluorine-containing aromatic silane coupling agent comprising a compound of the formula (1) wherein Y is $-CAB(CH_2)_mSi(CH_3)_nZ'_{3-n}$, wherein A, B, m and n are each as defined above, Z' is $OCH_3$ or $OC_2H_5$.

2. A finely divided magnetic material selected from the group consisting of magnetite, maghemite, samarium-cobalt and iron nitride powder, the magnetic material having its surface modified with the fluorine-containing aromatic silane coupling agent claimed in claim 1.

3. A magnetic fluid comprising the finely divided magnetic material of claim 2.

4. The magnetic fluid of claim 3, wherein said finely divided magnetic material is dispersed in a dispersion medium.

5. The magnetic fluid of claim 4, wherein said dispersion medium is a fluorine-containing oil.

6. The magnetic fluid of claim 3 further comprising a surfactant.

* * * * *

UNITED STATES PATENT AND TRADEMARK OFFICE
CERTIFICATE OF CORRECTION

PATENT NO.     : 5,741,922
DATED          : April 21, 1998
INVENTOR(S)    : Norio Yoshino Page 1 of 1

It is certified that error appears in the above-identified patent and that said Letters Patent is hereby corrected as shown below:

Column 12,
Line 31, please delete claim 1 in its entirety and substitute therefor:

-- 1. A fluorine-containing aromatic silane coupling agent comprising a compound of the formula (1)

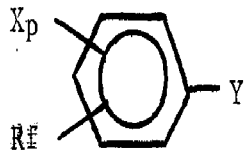

wherein X is H, F, Cl, $C_{1-20}$ alkyl or $C_{1-20}$ alkoxyl, p is an integer of 1 to 4, Y is -CAB $(CH_2)_m(CH_3)_nZ_{3-n}$, A and B are each H, or $CH_3$, Z is $OCH_3$ or $OC_2H_5$, and m and n are each 0 or 1, and RF is $C_{1-20}$ fluoroalkyl or $C_{1-100}$ fluoropolyether group. --

Signed and Sealed this

Sixteenth Day of September, 2003

JAMES E. ROGAN
*Director of the United States Patent and Trademark Office*